United States Patent
Fujihara et al.

(10) Patent No.: US 9,891,106 B2
(45) Date of Patent: Feb. 13, 2018

(54) TERAHERTZ WAVE SPECTROMETRY SYSTEM

(71) Applicant: Panasonic Intellectual Property Management Co., Ltd., Osaka (JP)

(72) Inventors: Seiji Fujihara, Osaka (JP); Yasuyuki Naito, Osaka (JP); Morio Tomiyama, Nara (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 0 days.

(21) Appl. No.: 15/488,522

(22) Filed: Apr. 17, 2017

(65) Prior Publication Data
US 2017/0336260 A1 Nov. 23, 2017

(30) Foreign Application Priority Data

May 19, 2016 (JP) .................. 2016-100079

(51) Int. Cl.
  *G01J 5/02* (2006.01)
  *G01J 3/28* (2006.01)
  *G01N 21/3581* (2014.01)

(52) U.S. Cl.
  CPC ............ *G01J 3/28* (2013.01); *G01N 21/3581* (2013.01); *G01J 2003/283* (2013.01); *G01N 2201/12* (2013.01)

(58) Field of Classification Search
  CPC . G01J 3/28; G01N 21/3581; G01N 2003/283; G01N 2201/12
  USPC ...................................................... 250/339.07
  See application file for complete search history.

(56) References Cited

U.S. PATENT DOCUMENTS

| | | | |
|---|---|---|---|
| 2006/0255277 A1* | 11/2006 | Cole | G01J 3/42 250/341.1 |
| 2012/0199743 A1 | 8/2012 | Cox et al. | |
| 2015/0316475 A1 | 11/2015 | Rahman et al. | |
| 2017/0254747 A1* | 9/2017 | Brady | G01N 21/3581 |

FOREIGN PATENT DOCUMENTS

| | | |
|---|---|---|
| JP | 2009-042207 | 2/2009 |
| JP | 2015-200532 | 11/2015 |

* cited by examiner

*Primary Examiner* — David Porta
*Assistant Examiner* — Meenakshi Sahu
(74) *Attorney, Agent, or Firm* — McDermott Will & Emery LLP

(57) ABSTRACT

Provided is a terahertz wave spectrometry system that is capable of easily identifying and quantitating an analyzing target molecule in an analyte, even if the analyte contains water, by calculating a baseline function expressing the absorption characteristic of water peculiar to the terahertz wave.

15 Claims, 12 Drawing Sheets

TERAHERTZ WAVE SPECTROMETRY SYSTEM

BACKGROUND

1. Technical Field

The present disclosure relates a terahertz wave spectrometry system.

2. Description of the Related Art

Recently, technologies applying electromagnetic waves in the terahertz (THz) frequency region (hereinafter referred to as terahertz waves) have been attracting attention. The terahertz waves are electromagnetic waves in a frequency range from about 0.1 THz to 30 THz. This frequency region is a boundary region between the light region and the radio wave region, and has been an unexplored region until recently. However, with the recent development of the femtosecond laser technologies, non-linear optical technologies, semiconductor device technologies, and so on, fundamental technologies regarding generation, detection and transmission of the terahertz waves have advanced, and applied technologies of the terahertz waves have been developed.

Since characteristic absorption spectrums of various substances can be acquired in the terahertz wave region, application of the absorption spectrums as fingerprint spectrums for molecular discrimination is expected. Particularly, natural vibration frequencies of biologically relevant molecules or organic molecules such as protein, fat and carbohydrate correspond to frequencies in the terahertz frequency region. For this reason, analyses of biologically relevant molecules, studies regarding cells and organic chemistry researches using the terahertz wave spectrometry technology have been attracting attention.

Water is a substance that easily absorbs the terahertz waves. Particularly, the absorbance of the terahertz waves by water increases monotonously as the frequency increases in a range from 0.1 THz to 10 THz. When an analyte contains water, a terahertz wave irradiating the analyte is absorbed mainly by water. In a case where an analyzing target molecule which has a characteristic absorption spectrum with respect to a terahertz wave co-exists with water, the absorption spectrum of water and the absorption spectrum of the analyzing target molecule overlap, so that it is sometimes difficult to distinguish the characteristic absorption spectrum. Because biologically relevant molecules such as protein, fat or carbohydrate often co-exist with water, there is a need for an easy method for detecting and identifying absorption spectrums inherent in such molecules.

PTL1 discloses a method of measuring components such as protein, fat, carbohydrate, and the like in seeds.

PTL2 discloses a method of correcting a baseline of a spectrum data acquired by a mass spectrometer or the like.

CITATION LIST

Patent Literature

PTL 1: Japanese Patent No. 5,429,657
PTL 2: Unexamined Japanese Patent Publication No. 2015-200532
PTL 3: United States Patent Application Publication No. 2006/0255277 A1
PTL 4: United States Patent Application Publication No. 2012/0199743 A1
PTL 5: United States Patent Application Publication No. 2015/0316475 A1

The inspection object in the method disclosed by PTL1 is a seed with a limited water content up to 10%. PTL1 describes that it is possible to analyze protein, fat, carbohydrate, or the like contained in the seed by irradiating the seed with a terahertz wave, and detecting a terahertz wave transmitted through the seed. PTL1 describes that absorption of the terahertz wave by water increases as the water content increases, and thus it becomes difficult to identify the spectrum of the substance to be analyzed. However, PTL1 is silent as to how to practically solve this problem. Also, PTL1 describes that the seed with a low water content shows a characteristic transmission spectrum depending on the substance contained in the seed, and thus it is possible to analyze protein, fat, carbohydrate, or the like contained in the seed. However, the value of the transmission spectrum varies depending on the quantity of the contained water. PTL1 is silent as to how to correct the spectrum depending on the water content.

PTL2 discloses a method of correcting a baseline of a spectrum data acquired by a mass spectrometer. PTL2 describes to set a line connecting bottoms in troughs adjacent to each peak of a spectrum on a peak by peak basis. Thus, it is necessary to set a plurality of baselines having individual functions in respective sections between bottoms of each acquired spectrum, so that a heavy load is put on computational processing. Since the terahertz wave absorption spectrum of water increases monotonously as the frequency increases, it is not necessary to set a plurality of baselines in each spectrum. Accordingly, it is desirable to correct a baseline without putting a heavy load on the computational processing.

SUMMARY

One non-limiting and exemplary embodiment provides a system that performs a method of identifying or quantitating an analyzing target molecule in an analyte, even if the analyte have various water content, by easy computational processing of an absorption spectrum acquired by irradiating the analyte with a terahertz wave.

In one general aspect, the techniques disclosed herein feature a terahertz wave spectrometry system comprising:
a terahertz wave emitter for emitting a terahertz wave to irradiate a test substance with the terahertz wave;
a light receiver that receives an absorbance of a terahertz wave transmitted through or reflected from the test substance; and
a signal processor,
wherein the signal processor, in operative,
outputs an irradiation signal to the terahertz wave emitter to irradiate the test substance with the terahertz wave while increasing or decreasing a frequency f of the terahertz wave,
acquires an intensity of the terahertz wave received by the light receiver;
acquires a function A(f) of an absorption spectrum expressing the absorbance of the terahertz wave which has been transmitted through or reflected from the test substance with respect to the frequency f, on the basis of an intensity of the terahertz wave emitted by the terahertz wave emitter and the intensity of the terahertz wave received by the light receiver;
differentiates the function A(f) with respect to the frequency f to acquire a function A'(f);

detects two or more first areas in each of which a value of the function A'(f) changes from a negative value to a positive value as the frequency f increases;

defines bottom frequencies b1, b2, . . . , bm as values of the frequency f each satisfying a formula (I) below in an m-th one of the first areas, where m is an integer of 2 or more;

$$\text{function } A'(bm) = 0 \tag{I}$$

calculates a value of the function A(bm) at each bottom frequency bm;

forms a baseline function B(f) passing through coordinates (b1, f(b1)), coordinates (b2, f(b2)), . . . , coordinates (bm, f(bm)), or a neighborhood of these coordinates; and subtracts the baseline function from the absorption spectrum.

The present disclosure provides a terahertz wave spectrometry system that makes it possible to easily identify and quantitate an analyzing target molecule in an analyte, even if the analyte contains water, and to facilitate visual comparison of measured results of a plurality of analytes.

Additional benefits and advantages of the disclosed embodiments will become apparent from the specification and drawings. The benefits and/or advantages may be individually acquired by the various embodiments and features of the specification and drawings, which need not all be provided in order to acquire one or more of such benefits and/or advantages.

It should be noted that general or specific embodiments may be implemented as a system, a method, an integrated circuit, a computer program, a storage medium, or any selective combination thereof.

DETAILED DESCRIPTION OF THE EMBODIMENTS

First Exemplary Embodiment

Figure 1:
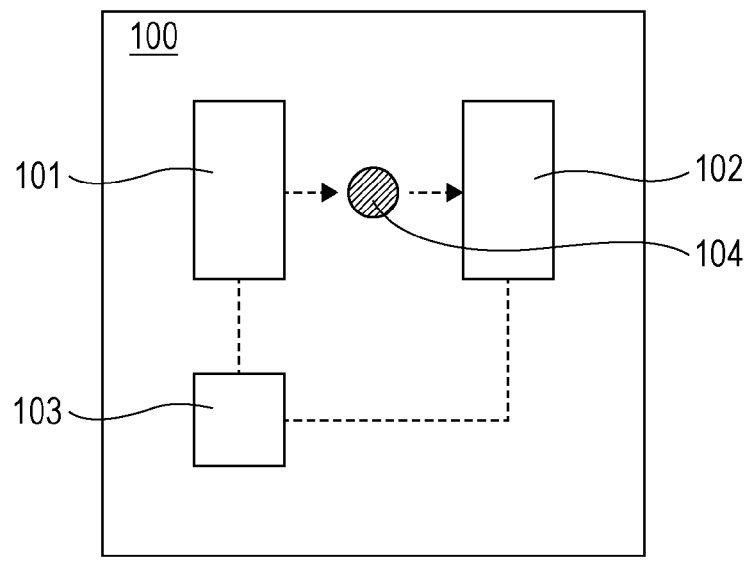
FIG. 1 is a schematic diagram illustrating terahertz wave spectrometry system 100 for transmission measurement in accordance with a first exemplary embodiment.

FIG. 1 is a schematic diagram illustrating terahertz wave spectrometry system 100 for transmission measurement in accordance with a first exemplary embodiment.

Terahertz wave spectrometry system 100 shown in FIG. 1 has a system configuration for measuring a terahertz wave transmitted through an analyte, and is configured by terahertz wave emitter 101, light receiver 102, and signal processor 103. Analyte 104 is placed on an optical axis between terahertz wave emitter 101 and light receiver 102.

As terahertz wave emitter 101 that generates a terahertz wave, such an terahertz wave emitter may be mainly used that generates a terahertz wave by irradiating a photoconductive element or a non-linear optical crystal with a femtosecond laser pulse having a pulse width in a range from several femtoseconds to several hundred femtoseconds. By using this kind of terahertz wave emitter, it is possible to utilize terahertz waves in a frequency range from 0.1 THz to 30 THz.

Analyte 104 is irradiated with the terahertz wave generated by terahertz wave emitter 101, and the terahertz wave transmitted through analyte 104 enters light receiver 102.

Light receivers used as light receiver 102 include a photoconductive element, a pyroelectric light receiver, a bolometer, and the like, which have a detection sensitivity in a wide wavelength range.

Also, although not shown in the figure, a light collection optical system configured by a lens or the like may be disposed between terahertz wave emitter 101 and analyte 104. The lens used may be made of a plastic material, such as polyethylene, through which terahertz waves can transmit.

An absorption spectrum of the analyte can be calculated by an arithmetic operation in signal processor 103 based on an oscillation intensity of a terahertz wave from terahertz wave emitter 101 and a detected intensity of a terahertz wave detected by light receiver 102. An absorbance at each frequency can be known from the calculated absorption spectrum.

Figure 2:
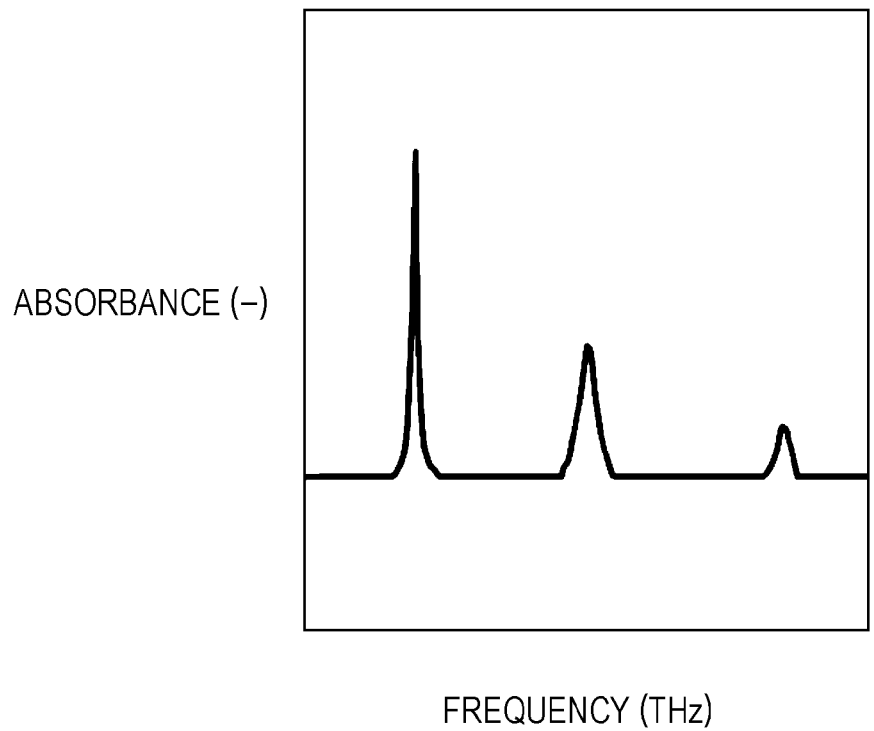
FIG. 2 is a graph showing an example of a terahertz wave absorption spectrum which can be a database of an analyzing target molecule.

FIG. 2 illustrates a schematic diagram showing an example of a terahertz wave absorption spectrum which can be a database of an analyzing target molecule. An absorption peak exhibiting a shape protruded upward is expressed as a specific absorbance at a frequency specific to an analyzing target molecule. Data expressing all these spectrum shapes are stored as a database in signal processor 103. An analyzing target molecule in the analyte can be identified by comparing an absorption spectrum of the analyte with the spectra stored in the database. Also, since the intensity of the absorption spectrum is proportional to the density of the analyzing target molecule in the analyte, the density of the analyzing target molecule can be quantitated.

Figure 3:
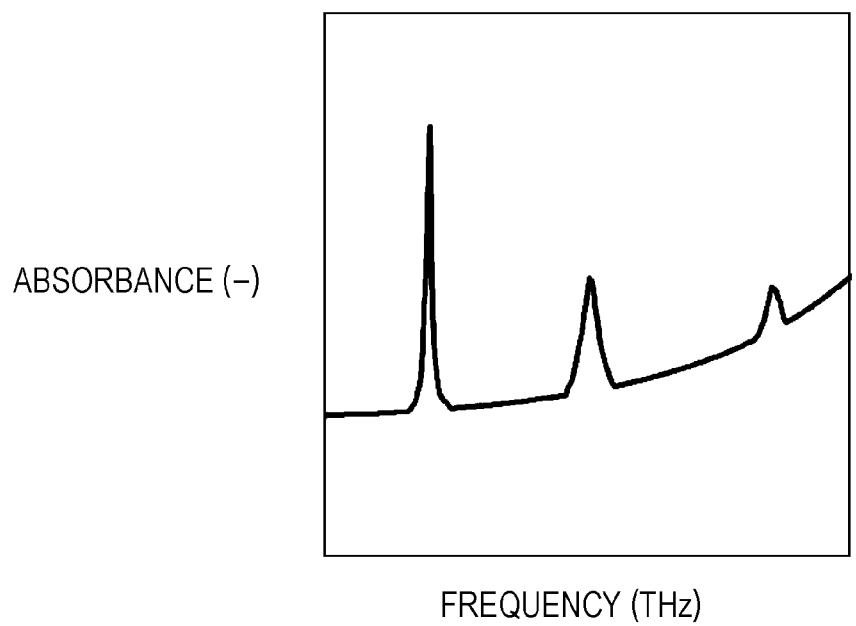
FIG. 3 is a graph showing an example of a terahertz wave absorption spectrum which can be acquired in a case where an analyzing target molecule and water are mixed.

FIG. 3 illustrates a schematic diagram expressing an example of a terahertz wave absorption spectrum which can be acquired in a case where an analyzing target molecule and water are mixed. Referring to FIG. 3, several absorption peaks each exhibiting a shape protruded upward are acquired similarly to FIG. 2, however, such an impression is given that the absorbance as a whole increases monotonously as the frequency increases. This is because the absorption spectrum of water is detected in addition to the absorption spectrum of the analyzing target molecule. The absorbance of water tends to monotonously increase as the frequency increases, particularly in a frequency range from 0.1 THz to 10 THz. Therefore, such a simple process is required that allows the spectrum shape as illustrated in FIG. 3 to be compared with the spectrum shape as illustrated in FIG. 2 stored in signal processor 103.

Figure 19:
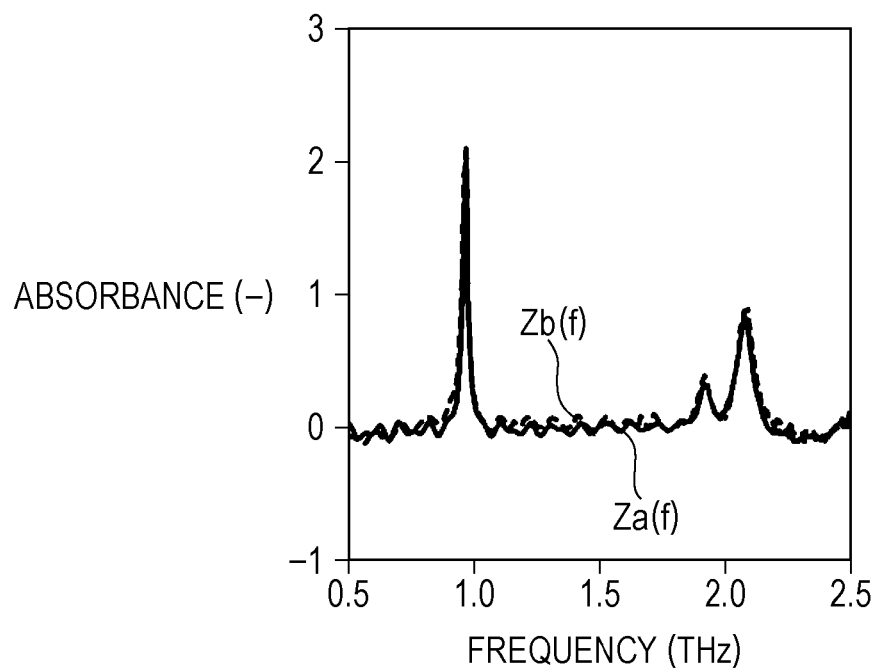
FIG. 19 is a graph showing a post-subtraction spectrum Za(f) of sample a, and a post-subtraction spectrum Zb(f) of sample b in Example 3.

The terahertz wave absorption spectrum as shown in FIG. 3 is also disclosed in PTL 3 (see FIG. 6 thereof), PTL 4 (see FIG. 2A thereof), and PTL 5 (see FIG. 19 thereof). It would be easy for a skilled person who has read these patent literatures to acquire the terahertz wave absorption spectrum as shown in FIG. 3.

Hereinafter, description will be made on a process of calculating a baseline function from an absorption spectrum, and subtracting the baseline function from the absorption spectrum to acquire a post-subtraction absorption spectrum.

Figure 4:
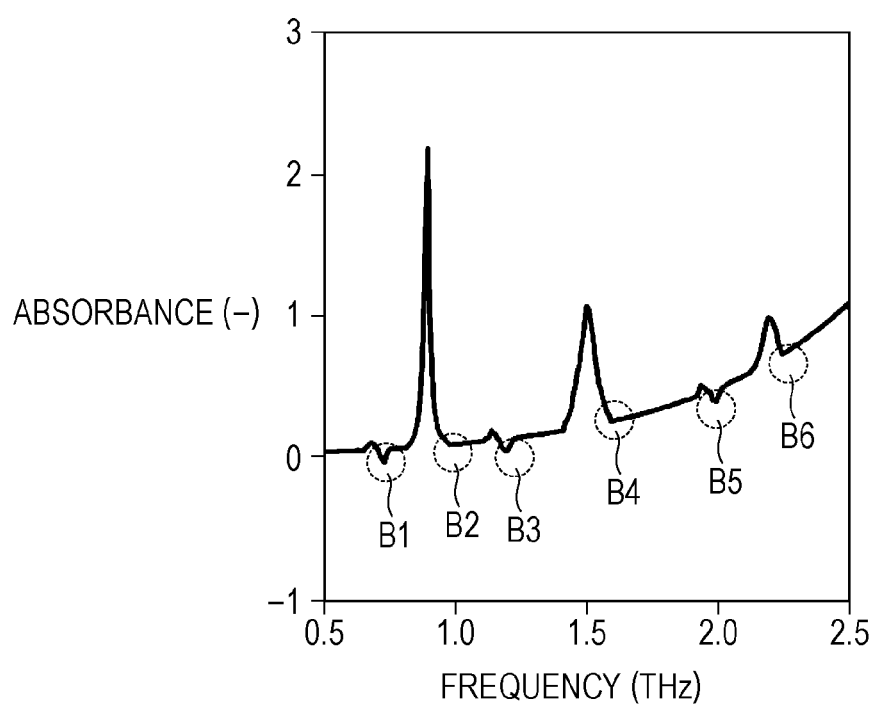
FIG. 4 is a graph showing an absorption spectrum A(f) and detected bottoms in accordance with the first exemplary embodiment.

First, signal processor 103 calculates an absorption spectrum $A(f)$ in a specified frequency range from a detected intensity and an oscillation intensity (FIG. 4).

To calculate a baseline function from the absorption spectrum, it is necessary to detect a bottom, or a point that is not included in the absorption peaks each expressed as a shape protruded upward.

A bottom may be detected by differentiating the absorption spectrum once to acquire a derivative (first-order derivative), or a gradient of the signal waveform, finding an area in which the derivative once becomes zero from a negative value (i.e., the signal waveform is a declivity waveform) and thereafter changes to a positive value (i.e., the signal waveform is an acclivity waveform), and setting as a bottom the position where the derivative becomes zero in the area. To acquire frequency values at which the values of the first-order derivative become zero, it is necessary to execute differentiation operations at a number of frequency values, so that the information processing load becomes large. To avoid the large information processing load, such a method may be used that finds an area in which the derivative changes from a negative value to a positive value, and a point in the area is determined as a bottom.

FIG. 4 illustrates a graph showing bottoms detected from an absorption spectrum $A(f)$. Points B1 to B6 are detected as bottoms, each of which exists in an area in which the first-order derivative changes from a negative value to a positive value.

Usually, the number of detected bottoms is m (m is an integer of 2 or more). Frequencies at bottoms B1, B2, ..., and Bm are defined as bottom frequencies b1, b2, ..., and bm, respectively. A function connecting the plurality of bottoms or their neighbor points may be approximated by an exponential function, values a and b satisfying the following formula may be acquired, and the function may be determined as a baseline function $B(f)$:

$$B(f) = a \cdot \exp[b \cdot f], f: \text{frequency}$$

Values a and b may be acquired by approximation using the least-square method or the like.

Specifically, a value of function $A(bm)$ at the bottom frequency bm is calculated. Next, the baseline function $B(f)$ passing through coordinates (b1, f(b1)), coordinates (b2, f(b2)), ..., and coordinates (bm, f(bm)) is formed. To form a smooth baseline function $B(f)$, at least a part of these coordinates may possibly be substituted by their neighborhood values.

Figure 5:
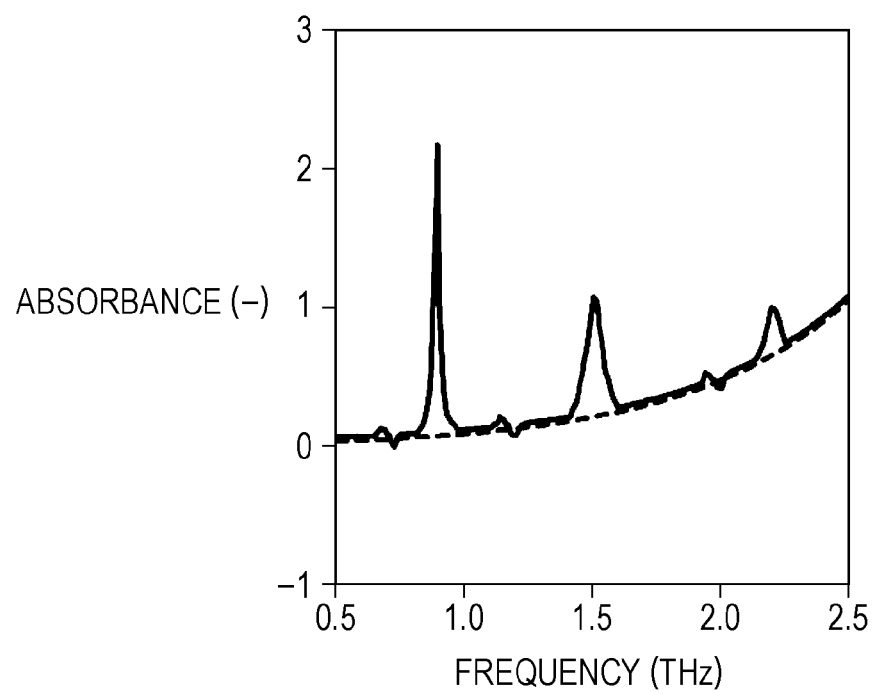
FIG. 5 is a graph showing the absorption spectrum A(f) and a baseline function B(f) in an overlapping manner in accordance with the first exemplary embodiment.

FIG. 5 illustrates a graph showing the absorption spectrum $A(f)$ and the baseline function $B(f)$ indicated in an overlapping manner. In FIG. 5, to form a smooth baseline function $B(f)$, coordinates (B2, A(B2)), coordinates (B4, A(B4)) and coordinates (B6, A(B6)) are used for the bottoms B2, B4 and B6, respectively. On the other hand, neighbor coordinates (B1', A(B1)') of coordinates (B1, A(B1)), neighbor coordinates (B3', A(B3)') of coordinates (B3, A(B3)) and neighbor coordinates (B5', A(B5)') of coordinates (B5, A(B5)) are used for the bottoms B1, B3 and B5, respectively, to form a smooth baseline function $B(f)$.

Although the baseline function is approximated by an exponential function in the present exemplary embodiment, it may be approximated by a quadratic function. Also in this case, the function can be calculated from a plurality of bottoms by using the least-square method or the like.

The baseline function $B(f)$ is subtracted from the acquired absorption spectrum $A(f)$ to acquire a post-subtraction spectrum $Z(f)$ as expressed by the following formula.

$$Z(f) = A(f) - B(f)$$

Figure 6:
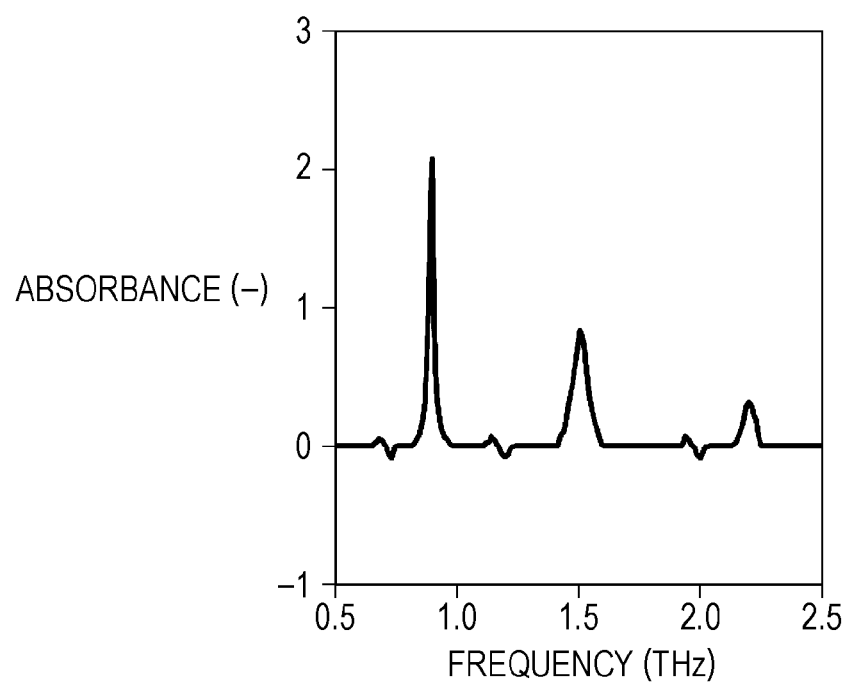
FIG. 6 is a graph showing a post-subtraction spectrum Z(f) in accordance with the first exemplary embodiment.

FIG. 6 illustrates the post-subtraction spectrum $Z(f)$. An analyzing target molecule can be identified or quantitated by comparing the post-subtraction spectrum $Z(f)$ with the absorption spectrums stored in the database.

To calculate the baseline function $B(f)$, it is not necessary to set all of the detected bottoms, but at least two bottoms, preferably three or more bottoms, may be set.

It is desirable that the range of the set bottoms is wide. Among the bottoms detected in the measuring frequency range, a bottom at the minimum frequency is set as a minimum frequency bottom, and a bottom at the maximum frequency is set as a maximum frequency bottom. The baseline function $B(f)$ may be calculated using at least these two points. In this manner, a baseline function $B(f)$ approximating the baseline in a wide range can be calculated.

A bottom located in the intermediate of the minimum frequency bottom and the maximum frequency bottom may be set as an intermediate bottom, and a more accurate baseline function B(f) may be calculated using at least the minimum frequency bottom, the maximum frequency bottom and the intermediate bottom.

Since it is desirable that the measuring frequency range is set to a wide range, it is desirable to set a frequency range of at least 1 THz in the range from 0.5 THz to 10 THz.

Although the transmission measurement has been described hereinabove, the same effects can be acquired by measuring a reflection intensity of a terahertz wave reflected from the analyte.

Figure 7:
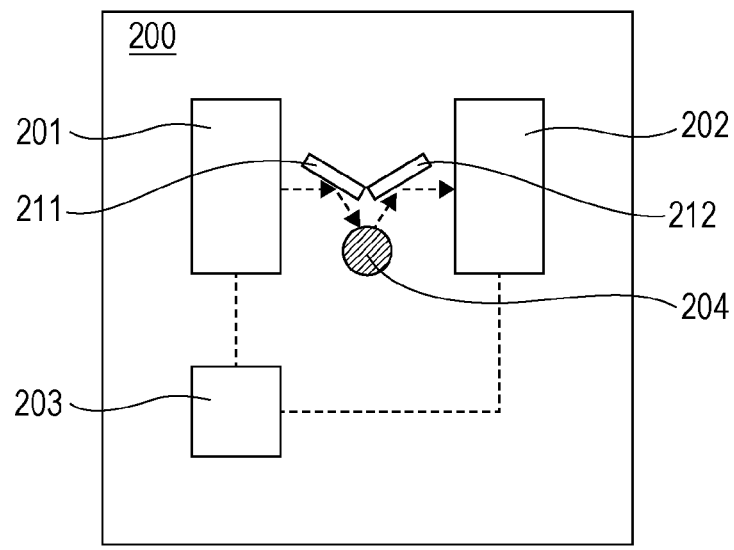
FIG. 7 is a schematic diagram illustrating terahertz wave spectrometry system 200 for reflection measurement in accordance with the first exemplary embodiment.

Hereinafter, description will be made on a case of the reflection measurement. FIG. 7 is a schematic diagram illustrating terahertz wave spectrometry system 200 for reflection measurement. The reflection-type spectrometry system shown in FIG. 7 is configured by terahertz wave emitter 201, light receiver 202, signal processor 203, oscillation-side mirror 211, and detection-side mirror 212. A terahertz wave generated from terahertz wave emitter 201 is reflected by oscillation-side mirror 211 to irradiate analyte 204. A terahertz wave reflected from analyte 204 is reflected by detection-side mirror 212 to enter light receiver 202.

Also in the case of the reflection measurement, in the same manner as the transmission measurement, an absorbance of analyte 204 can be calculated in signal processor 203 by an arithmetic operation on an intensity of the terahertz wave generated by terahertz wave emitter 201 and an intensity of the terahertz wave detected by light receiver 202.

Also in the case of the reflection measurement, in the same manner as the transmission measurement, an absorption spectrum which is free from influence of water and thus is peculiar to the analyzing target molecule can be acquired by calculating a baseline function $B_{ref}(f)$ from the acquired absorption spectrum $A_{ref}(f)$ and subtracting the baseline function $B_{ref}(f)$ from the absorption spectrum $A_{ref}(f)$ to acquire a post-subtraction spectrum $Z_{ref}(f)$. Accordingly, an analyzing target molecule in the analyte can be identified or the density of the analyzing target molecule can be determined.

Figure 22:
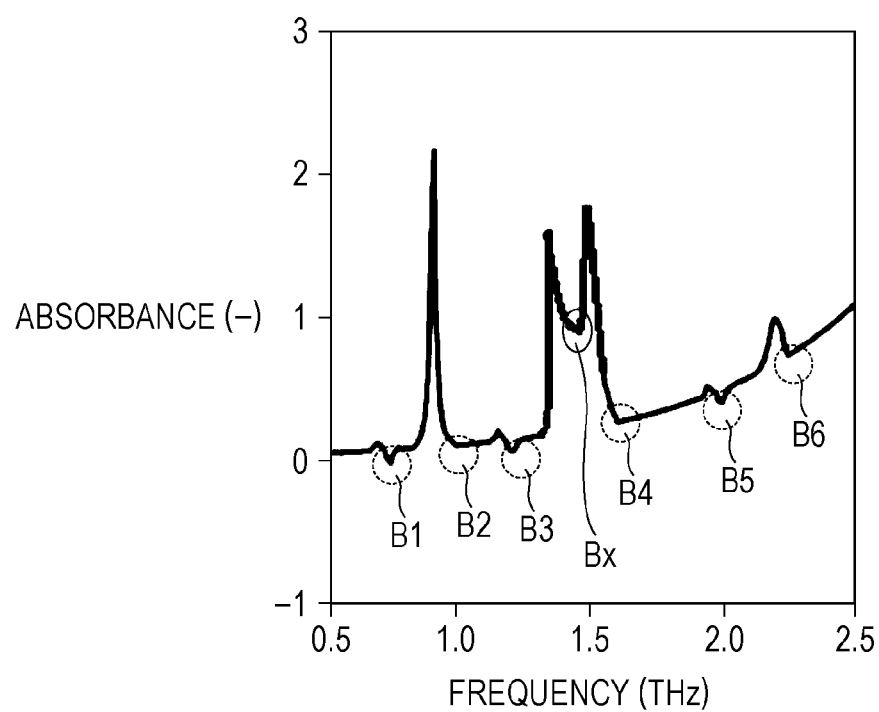
FIG. 22 is a graph showing an absorption spectrum A(f) having an absorption peak including a bottom Bx.

In a case where an absorption peak includes a bottom Bx as shown in FIG. 22, the bottom Bx is excluded from the bottoms used for forming the baseline function B(f). In other words, coordinates (bs, f(bs)) are excluded when the baseline function B(f) is formed.

If such a condition is satisfied that values of the absorption spectrums A(Bs−1) and A(Bs) at two adjacent bottoms Bs−1 and Bs (s is an integer from 2 to m), respectively, are equal to or larger than a predetermined value c, it is determined that the bottom Bs is included in an absorption peak. In this case, the bottom Bs having coordinates (bs, f(bs)) is excluded from the bottoms for forming the baseline function B(f). Next, it is similarly determined whether or not values of the absorption spectrums A(Bs−1) and A(Bs+1) at the two bottoms Bs−1 and Bs+1, which are adjacent to each other by ignoring the bottom Bs, are equal to or larger than the predetermined value c.

Second Exemplary Embodiment

More accurate identification is possible by setting a bottom which is closer to an absorption peak as a bottom for calculating the baseline function B(f). Particularly, it is desirable to set as an absorption bottom a bottom of a portion landed on the baseline after an absorption peak, and to calculate the baseline function B(f) from this absorption bottom. A method of setting the absorption peaks and the absorption bottoms will hereinafter be described.

A peak may be determined by differentiating the absorption spectrum once to acquire a derivative (a first-order derivative), finding an area in which the derivative once changes from a positive value to zero and thereafter changes to a negative value, and setting as a peak the position where the derivative becomes zero in the area. To acquire frequency values at which the values of the first-order derivative become zero, it is necessary to execute differentiation operations at a number of frequency values, so that the information processing load becomes large. To avoid the large information processing load, such a method may be used that finds an area in which the derivative changes from a positive value to a negative value, and a point in the area is determined as a peak.

Figure 8:
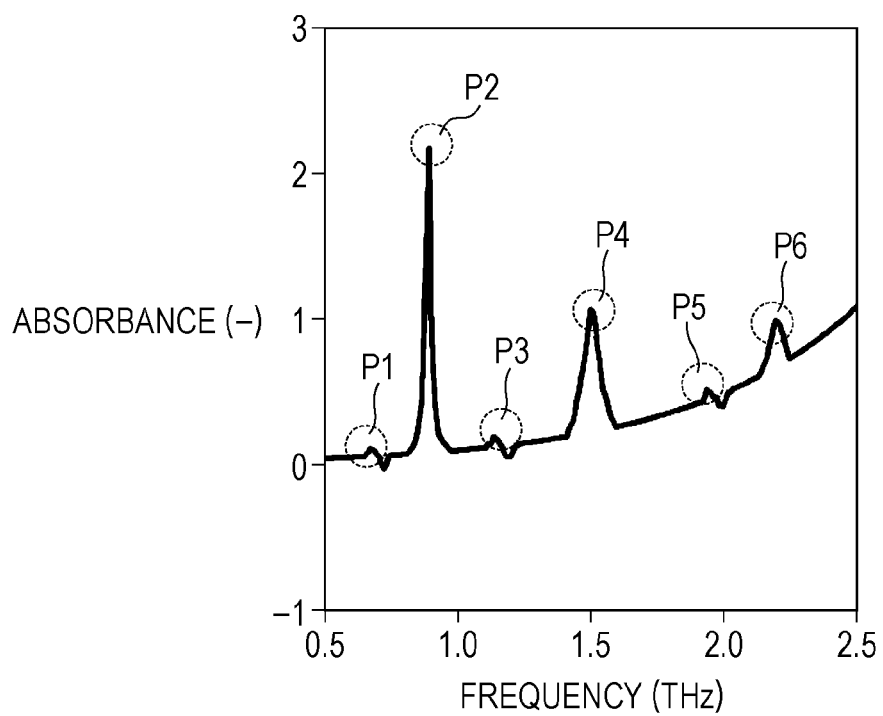
FIG. 8 is a graph showing an absorption spectrum A(f) and detected peaks in accordance with the first exemplary embodiment.

FIG. 8 illustrates peaks detected from an absorption spectrum. Detected peaks are P1 to P6, each of which is in an area where the first-order derivative changes from a negative value to a positive value.

The peaks include those affected by minute concave and convex waveforms caused by noises or the like. An absorbance difference between each peak of the concave-convex shape and an adjacent bottom is calculated, and a peak at which the absorbance difference from an adjacent bottom is equal to or larger than a predetermined value is determined as an absorption peak. For example, a peak may be determined as an absorption peak if the absorbance difference from an adjacent bottom is equal to or larger than 0.2, and as a peak caused by a noise if the absorbance difference from an adjacent bottom is smaller than 0.2. The predetermined value may not necessarily be limited to 0.2, and may appropriately be set considering the sensitivity of the light receiver, the conditions of the analyte, or the like.

Figure 9:
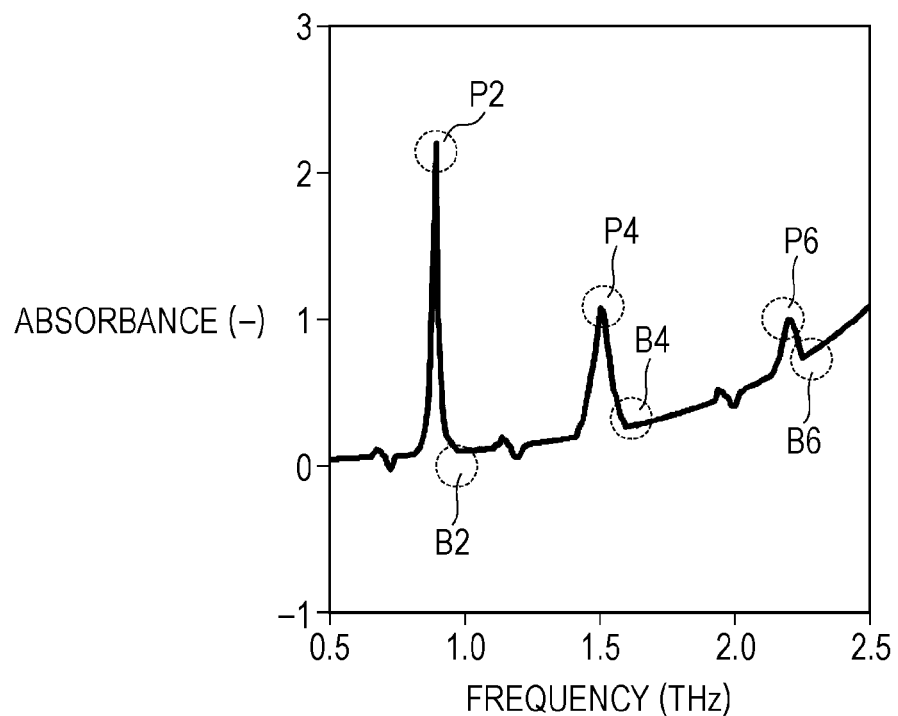
FIG. 9 is a graph showing absorption peaks and absorption bottoms in accordance with the first exemplary embodiment.

Next, each bottom adjacent to an absorption peak is determined as an absorption bottom. FIG. 9 shows absorption peaks and absorption bottoms in a case where a peak having the absorbance difference from an adjacent bottom equal to or larger than 0.2 is determined as an absorption peak. Absorption peaks are P2, P4 and P6, and absorption bottoms are B2, B4 and B6. From these absorption bottoms, a baseline function B(f) may be calculated.

It is not necessary that all of the bottoms for calculating the baseline function are absorption bottoms, but the bottoms for calculating the baseline function may be a mixture of absorbance bottoms and other bottoms.

To eliminate the influence of the minute concave and convex waveforms caused by noises or the like, smoothing processing may be performed. That is, each bottom may be averaged from values of the previous and next bottoms, before executing the operation of determining the absorption bottoms.

It is desirable that the measuring frequency range is set to include absorption bottoms.

Third Exemplary Embodiment

Figure 10:
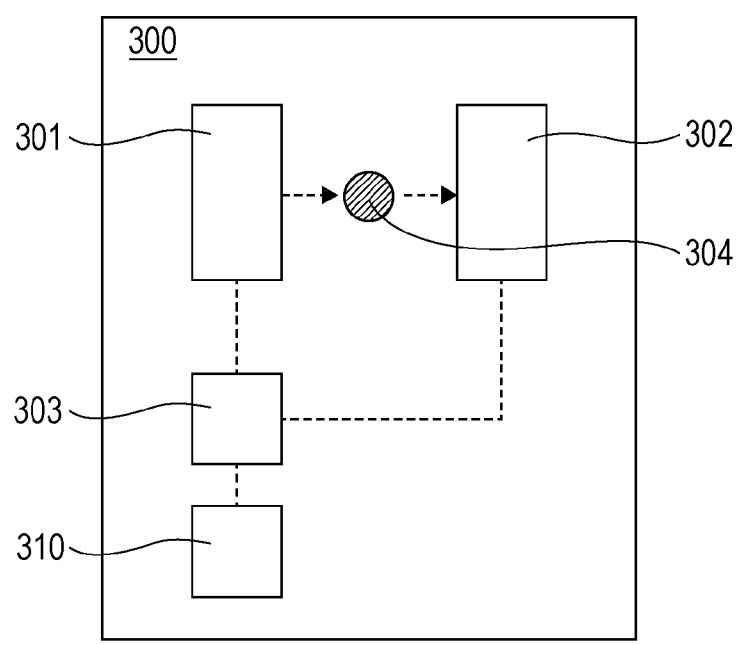
FIG. 10 is a schematic diagram illustrating terahertz wave spectrometry system 300 for transmission measurement in accordance with a third exemplary embodiment.

FIG. 10 is a schematic diagram illustrating terahertz wave spectrometry system 300 for transmission measurement in accordance with a third exemplary embodiment.

Terahertz wave spectrometry system 300 shown in FIG. 10 has a system configuration for measuring a terahertz wave transmitted through an analyte, and is configured by terahertz wave emitter 301, light receiver 302, and signal processor 303. Analyte 304 is placed on an optical axis between terahertz wave emitter 301 and light receiver 302.

As a difference from the first exemplary embodiment, the present exemplary embodiment is featured by being provided with display unit 310 that is capable of displaying an absorption spectrum of analyte 304.

In the present exemplary embodiment, in the same manner as in the first exemplary embodiment, analyte 304 is irradiated with a terahertz wave generated by terahertz wave emitter 301, and a terahertz wave transmitted through analyte 304 enters light receiver 302. An absorbance of analyte 304 can be calculated by an arithmetic operation in signal processor 303 based on an oscillation intensity of the terahertz wave generated from terahertz wave emitter 301 and a detected intensity of the terahertz wave detected by light receiver 302. Also, an absorption spectrum, expressed as an absorbance with respect to frequency, can be calculated in a specified frequency area, and can be stored in a memory.

In the third exemplary embodiment, display unit 310 can display a post-subtraction spectrum $Z(f)$, which is calculated in signal processor 303 by calculating a baseline function $B(f)$ from an absorption spectrum $A(f)$ and then subtracting the baseline function $B(f)$ from the absorption spectrum $A(f)$.

Since signal processor 303 can store the post-subtraction spectrums $Z(f)$ of a plurality of analytes, it is also possible by display unit 310 to display the post-subtraction spectrums $Z(f)$ of the plurality of analytes in an overlapped manner. Since the baselines of the post-subtraction spectrums $Z(f)$ of the plurality of analytes can be displayed in an overlapped manner, the results can be visually compared. Since the absorption spectrums of analytes having different water content from one another are usually different from one another in the increase of the overall absorbance as the frequency increases, the absorption spectrums $A(f)$ exhibit different baselines from one another. Therefore, if the displayed baselines acquired as a plurality of measurement results are overlapped, it means that all the results are those acquired through processing of the subtracting operation.

It is also possible to display a plurality of post-subtraction absorption spectrums $Z(f)$ in parallel.

Values acquired by subtracting the baseline function $B(f)$ from the absorption spectrum $A(f)$ may be displayed.

Display unit 310 may display the absorption spectrum $A(f)$ or the baseline function $B(f)$.

Display unit 310 may display the absorption bottoms or the bottoms used to calculate the baseline function $B(f)$.

Although the transmission measurement has been described hereinabove, the same effects can be acquired by measuring a reflection intensity of a terahertz wave reflected from the analyte.

Fourth Exemplary Embodiment

Figure 23:
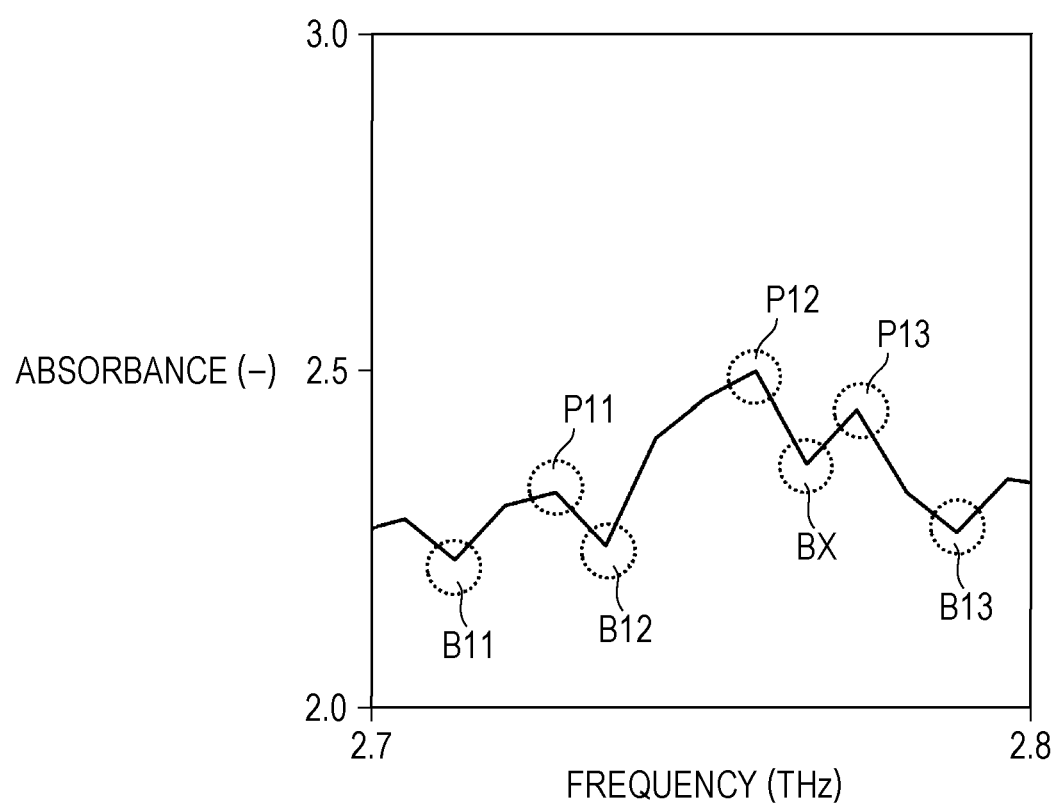
FIG. 23 is a graph showing absorption peaks and absorption bottoms in accordance with a fourth exemplary embodiment.

In a case where an absorption peak includes a bottom Bx as shown in FIG. 23, the bottom Bx is excluded from the bottoms used for forming the baseline function $B(f)$. In other words, coordinates (bs, f(bs)) are excluded when the baseline function $B(f)$ is formed.

If such a condition is satisfied that a difference between values of the absorption spectrum A(Bs−1) and the absorption spectrum A(Bs) at two adjacent bottoms Bs−1 and Bs (s is an integer from 2 to m), respectively, is equal to or larger than a predetermined value c, it is determined that the bottom Bs is included in an absorption peak. In this case, the bottom Bs having coordinates (bs, f(bs)) is excluded from the bottoms for forming the baseline function $B(f)$. Next, it is similarly determined whether or not a difference between values of the absorption spectrums A(Bs−1) and A(Bs+1) at two bottoms Bs−1 and Bs+1, which are adjacent to each other by ignoring the bottom Bs, are equal to or larger than the predetermined value c.

In a case where the predetermined value c is set, for example, to 0.1 in FIG. 23, values of A(B12) and A(Bx) are compared with each other, and the difference between the compared values is found to be larger than 0.1, so that the bottom Bx is excluded from the bottoms for forming the baseline function $B(f)$. Next, values of A(B12) and A(B13) are compared with each other, and the difference between the compared values is found to be smaller than 0.1, so that at least one of the bottom B12 and the bottom B13 is used to form the baseline function $B(f)$.

Although an example has been described in which the predetermined value c is set to 0.1, the value c may not necessarily be 0.1, and may appropriately be set considering the sensitivity of the light receiver, the conditions of the analyte, or the like.

Fifth Exemplary Embodiment

In a case where an absorption peak includes a bottom Bx as shown in FIG. 23, the bottom Bx is excluded from the bottoms used for forming the baseline function $B(f)$. In other words, coordinates (bs, f(bs)) are excluded when the baseline function $B(f)$ is formed.

If such a condition is satisfied that, after setting as a peak each point at which the derivative changes from a negative value to a positive value, a difference between values of the absorption spectrums A(Ps−1) and A(Ps) at two adjacent peaks Ps−1 and Ps (s is an integer from 2 to m), respectively, is smaller than a predetermined value d, it is determined that the bottom Bs located between peak Ps−1 and peak Ps is not included in an absorption peak. In this case, the bottom Bs having coordinates (bs, f(bs)) is excluded from the bottoms for forming the baseline function $B(f)$. Next, it is determined whether or not a difference between a larger one of the values of the absorption spectrums A(Ps−1) and A(Ps) and a value of an absorption spectrum A(Ps+1) at peak Ps+1 is smaller than the predetermined value d.

Referring to FIG. 23, in a case where the predetermined value d is set, for example, to 0.1, values of A(P12) and A(P13) are compared with each other, and the difference between the compared values is found to be smaller than 0.1, so that the bottom Bx between A(P12) and A(P13) is excluded. Next, the value of A(P12), which is a larger one of the values of A(P12) and A(P13), is compared with the value of A(P14), and the difference between the compared values is found to be larger than 0.1, so that a baseline function $B(f)$ is formed by using the bottom B13.

Although an example has been described in which the predetermined value d is set to 0.1, the value d may not necessarily be 0.1, and may appropriately be set considering the sensitivity of the light receiver, the conditions of the analyte, or the like.

Sixth Exemplary Embodiment

As shown in FIG. 23, if an absorption peak does not have a width that is equal to or larger than a predetermined width, the bottom B11 adjacent to the absorption peak is excluded from the bottoms for forming the baseline function $B(f)$. In other words, either coordinates (b11, f(b11)) or coordinates (b12, f(b12)) are excluded when the baseline function $B(f)$ is formed. It should be noted that, in a case where the difference between the values of the absorption spectrums A(Bs−1) and A(Bs) is equal to or larger than the predetermined value c, the bottom Bs is determined to be included in the absorption peak, so that the width of the absorption peak is not formed by this bottom.

If such a condition is satisfied that a difference between values of the absorption spectrums A(Bs−1) and A(Bs) at two adjacent bottoms Bs−1 and Bs (s is an integer from 2 to m), respectively, is smaller than a predetermined value c, a difference between bs−1 of coordinates (bs−1, f(bs−1)) at the absorption spectrum A(Bs−1) and bs of coordinates (bs, f(bs)) at the absorption spectrum A(Bs) is set as an absorption peak width. If the absorption peak width is equal to or larger than a predetermined width e, a baseline function B(f) is formed by using either the absorption spectrum A(Bs−1) or the absorption spectrum A(Bs).

Referring to FIG. 23, in a case where the predetermined value c is set, for example, to 0.1 and the predetermined value e is set, for example, to 0.05, values of A(B11) and A(B12) are compared with each other, and the difference between the compared values is found to be smaller than 0.1, so that a difference between b11 of coordinates (b11, A(b11)) at the absorption spectrum A(B11) and b12 of coordinates (b12, A(b12)) at the absorption spectrum A(B12) is set as an absorption peak width. Since this absorption peak width is smaller than 0.05, it is not determined that a baseline function B(f) may be formed by using either the bottom B11 or the bottom B12.

Next, the values of A(B12) and A(Bx) are compared with each other, and the difference between the compared values is found to be larger than 0.1, so that the bottom Bx is excluded. Next, the values of A(B12) and A(B13) are compared with each other, and the difference between the compared values is found to be smaller than 0.1, so that a difference between b12 of coordinates (b12, A(b12)) at the absorption spectrum A(B12) and b13 of coordinates (b13, A(b13)) at the absorption spectrum A(B13) is set as an absorption peak width. Since this absorption peak width is larger than 0.05, it is determined that a baseline function B(f) may be formed by using at least one of the bottom B12 and the bottom B13.

Although an example has been described in which the predetermined value c is set to 0.1 and the predetermined value e is set to 0.05, the values of c and e may not necessarily be 0.1 and 0.05, respectively, and may appropriately be set considering the sensitivity of the light receiver, the conditions of the analyte, or the like.

The signal processor (circuitry) may be configured by one or more electronic circuits including a semiconductor device, a semiconductor integrated circuit (IC) or a large scale integration (LSI). The LSI or IC may be integrated on a single chip or may be configured by combining a plurality of chips. For example, functional blocks except for storage elements may be integrated on a single chip. The circuits called LSI or IC herein may be called by another name depending on the degree of integration, and may be what may be called a system LSI, a VLSI (very large scale integration) or a ULSI (ultra large scale integration). Other circuits that may be used for the same purpose include a field programmable gate array (FPGA), which is programmed after being manufactured, or a reconfigurable logic device, which is designed such that it is possible to reconfigure connections within an LSI or to set up circuit blocks within an LSI.

Each of the steps performed in the signal processor may be implemented by a software processing included in a computer. In this case, the software may be stored in one or more non-transitory storage medium such as a ROM, an optical disk, or a hard disk drive, and may be executed by a processor such as a computer so that functions specified in the software can be performed by the processor and peripherals devices. The system or apparatus may have one or more non-transitory storage mediums having stored therein a software, one or more processors, and other necessary hardware devices such as an interface, for example.

EXAMPLES

Example 1

Tyrosine was mixed with polyethylene powder, and water was added to the mixture to produce an analyte containing water. Tyrosine was identified and quantitated from a terahertz wave absorption spectrum of the analyte. Since polyethylene is highly transparent to terahertz waves, and does not affect the absorption spectrum of the analyzing target molecules, polyethylene is used as an admixture of an analyte or as a base material for holding a sample.

The analyte was produced as described below. Polyethylene powder and tyrosine powder were mixed at a weight ratio of 1:1, then water was added to the mixture at a weight ratio of 1% relative to all powders, and the powders and the added water were uniformly mixed to produce an analyte.

A part of the analyte was spread on a sample holder made of a polyethylene plate (10 mm in diameter) so as to have a uniform thickness. The sample holder was configured by surrounding the polyethylene plate by a metal ring so that the diameter of the polyethylene plate within the ring became 10 mm. The step formed by the surface of the polyethylene plate and the metal ring allows the powder to be easily retained on the surface of the polyethylene plate.

Figure 11:
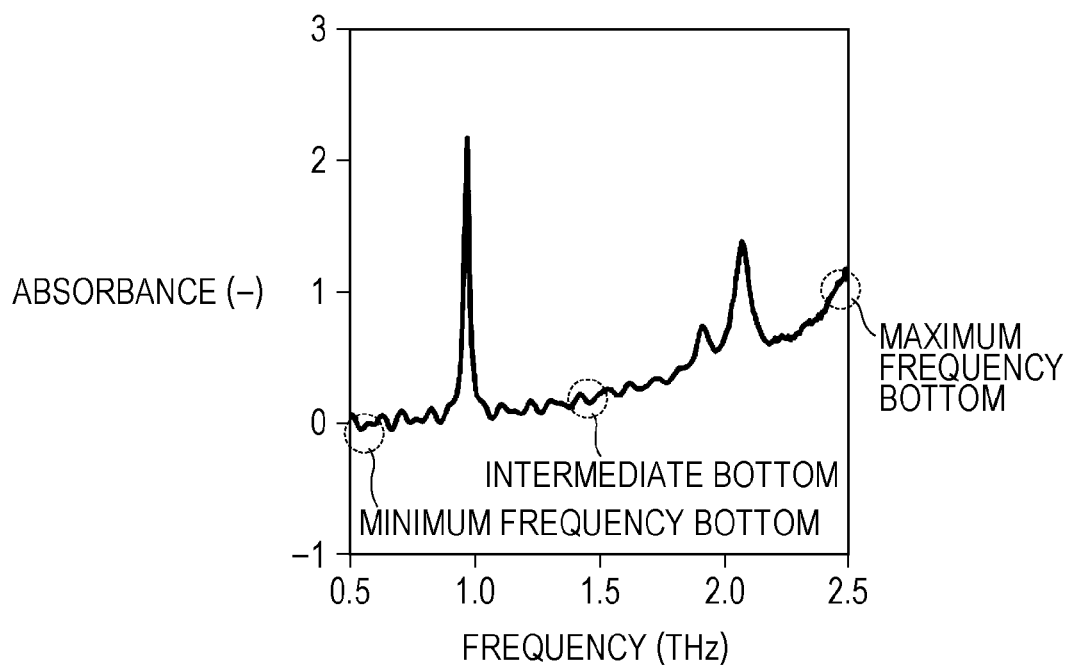
FIG. 11 is a graph showing an absorption spectrum A(f), a minimum frequency bottom, a maximum frequency bottom, and an intermediate bottom in Example 1.

An absorption spectrum was calculated by irradiating the analyte spread on the sample holder with a terahertz wave (irradiation spot of 3 mm in diameter) from the above, and detecting a terahertz wave transmitted through the analyte and the sample holder. A result of an absorption spectrum A(f) calculated in a frequency range from 0.5 THz to 2.5 THz is shown in FIG. 11. The absorption spectrum showed a tendency that the absorbance as a whole monotonously increased as the frequency increased.

An absorption spectrum A(f) was differentiated once to calculate a derivative, a part of each area in which the derivative changed from a negative value to a positive value was determined as a bottom.

Three bottoms, i.e., a minimum frequency bottom, a maximum frequency bottom and an intermediate bottom were selected in the frequency range from 0.5 THz to 2.5 THz, which is the measuring frequency range of the present exemplary embodiment. The selected points are also shown in FIG. 11.

By using the three selected bottoms, a baseline function B(f) as an exponential function was acquired by the least-square method as expressed by the formula shown below.

$$B(f)=0.0077 \cdot \exp[2.0 \cdot f] f\text{:frequency}$$

Figure 12:
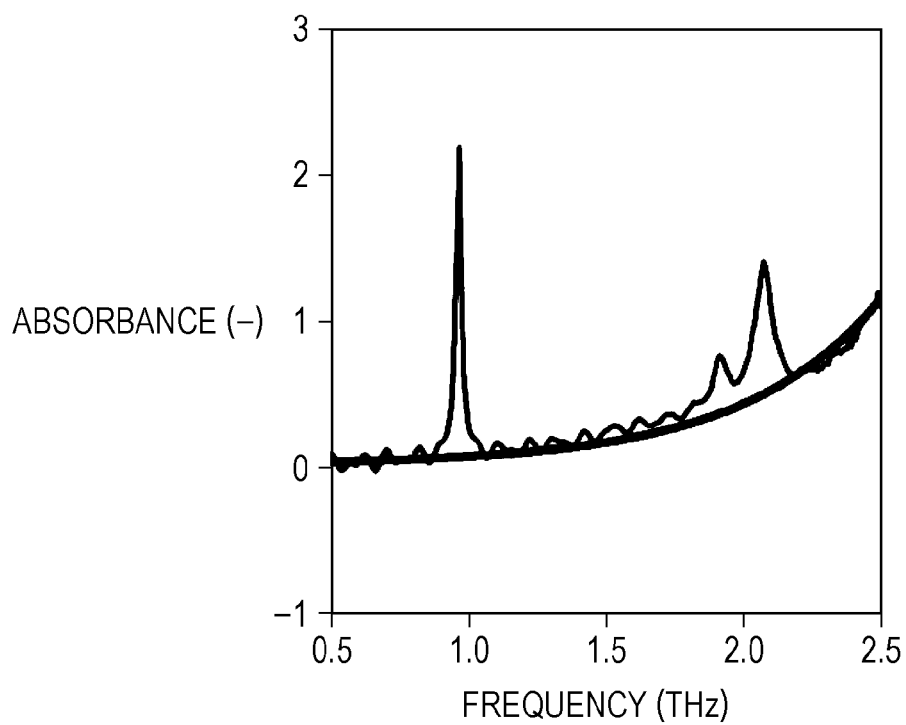
FIG. 12 is a graph showing the absorption spectrum A(f) and a baseline function B(f) in Example 1.

The absorption spectrum A(f) and the calculated baseline function B(f) are shown in FIG. 12.

Figure 13:
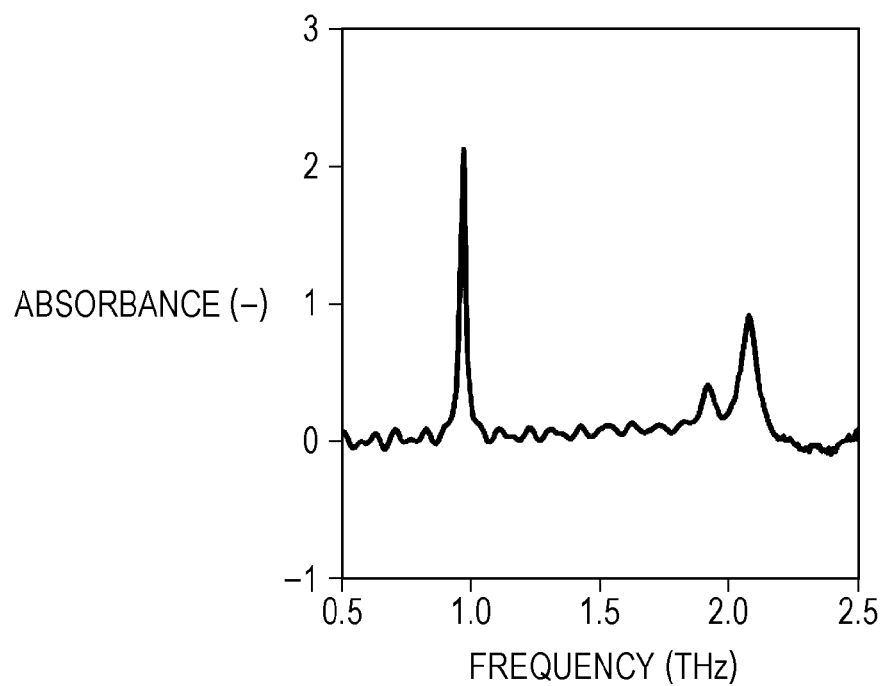
FIG. 13 is a graph showing a post-subtraction spectrum Z(f) in Example 1.

Next, a post-subtraction spectrum Z(f) was calculated by subtracting the baseline function B(f) from the absorption spectrum A(f). The result is shown in FIG. 13. Tyrosine in the analyte was identified from the post-subtraction spectrum Z(f). Also, a tyrosine content in the analyte was quantitated with an average error of 1.2%.

Example 2

In this Example, a baseline function B(f) was calculated by calculating absorption bottoms.

An absorption spectrum A(f) acquired from an analyte similar to that of Example 1 was differentiated once to calculate a derivative, and a part of each area in which the derivative changes from a negative value to a positive value was set as a bottom.

Also, a part of each area in which the derivative changes from a positive value to a negative value was set as a peak.

Figure 14:
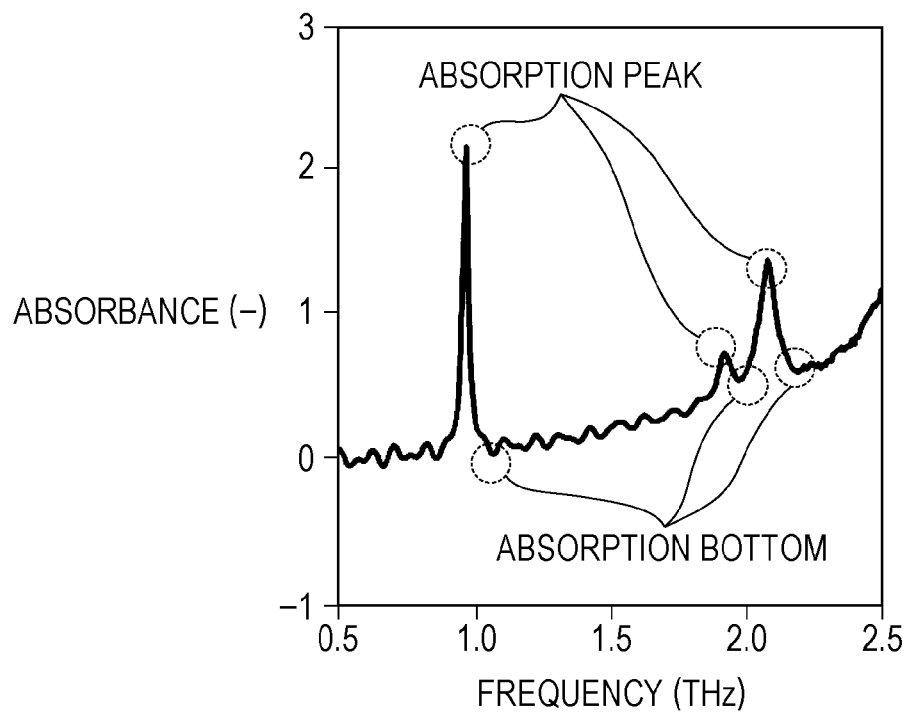
FIG. 14 is a graph showing an absorption spectrum A(f), absorption peaks, and absorption bottoms in Example 2.

Next, if a difference between an absorbance at a peak and an absorbance at a bottom adjacent to the peak on the higher frequency side was equal to or larger than 0.2, the peak was set as an absorption peak and the bottom was set as an absorption bottom. The thus set absorption peaks and absorption bottoms are shown in FIG. 14.

By using three absorption bottoms in a frequency range from 0.5 THz to 2.5 THz, which was a measuring frequency range of the present Example, a baseline function B(f) as an exponential function was acquired by the least-square method as expressed by the formula shown below.

$$B(f)=0.022 \cdot \exp[1.6 \cdot f] f : \text{frequency}$$

Figure 15:
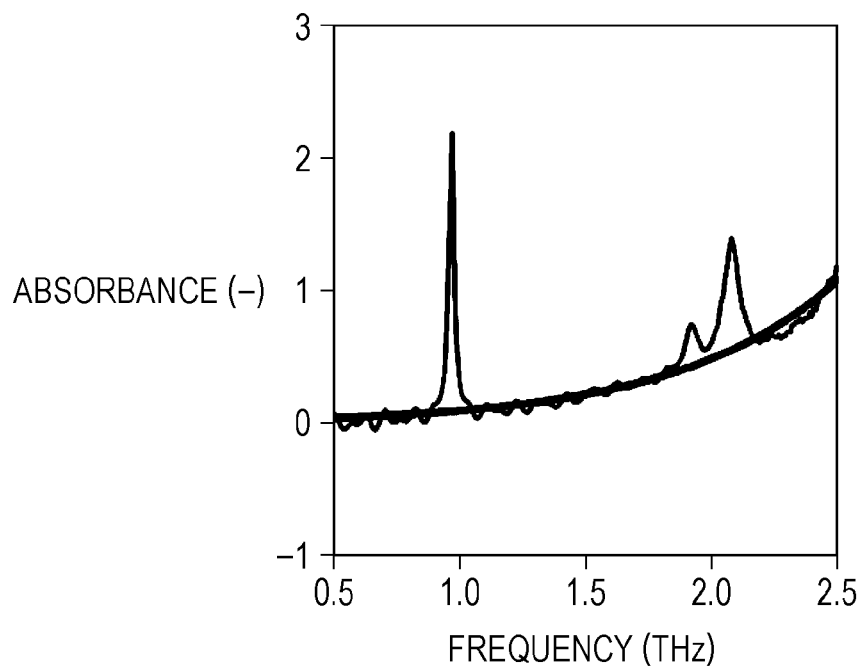
FIG. 15 is a graph showing the absorption spectrum A(f) and a baseline function B(f) in Example 2.

The absorption spectrum A(f) and the baseline function B(f) are shown in FIG. 15.

Figure 16:
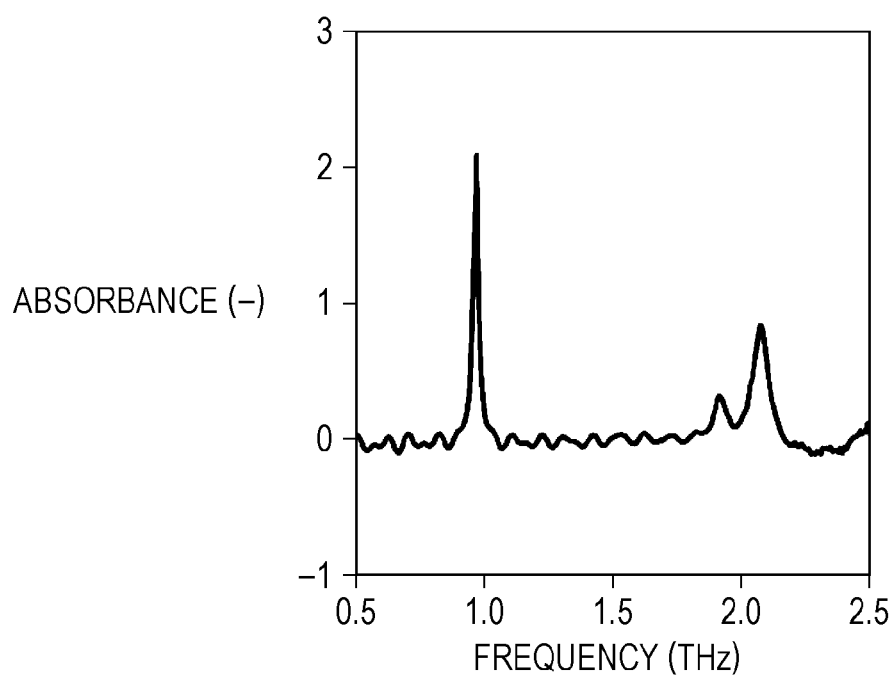
FIG. 16 is a graph showing a post-subtraction spectrum Z(f) in Example 2.

Next, a post-subtraction spectrum Z(f) was calculated by subtracting the baseline function B(f) from the absorption spectrum A(f). The calculation result is shown in FIG. 16. Tyrosine in the analyte was identified from the post-subtraction spectrum Z(f). Also, a tyrosine content in the analyte was quantitated with an average error of 1.2%.

Example 3

Tyrosine was mixed with polyethylene powder, and water was added to the mixture to produce an analyte. In the present Example, two kinds of analytes having different water content from one another were produced, and a terahertz wave absorption spectrum of each analyte was measured.

The analytes were produced as described below. Polyethylene powder and tyrosine powder were mixed at a weight ratio of 1:1, then water was added to the mixture at a weight ratio of 1% relative to all powders, and the powders and the added water were uniformly mixed to produce sample a. On the other hand, water was added to the mixture at a weight ratio of 3% relative to all powders, and the powders and the added water were uniformly mixed to produce sample b.

Figure 17:
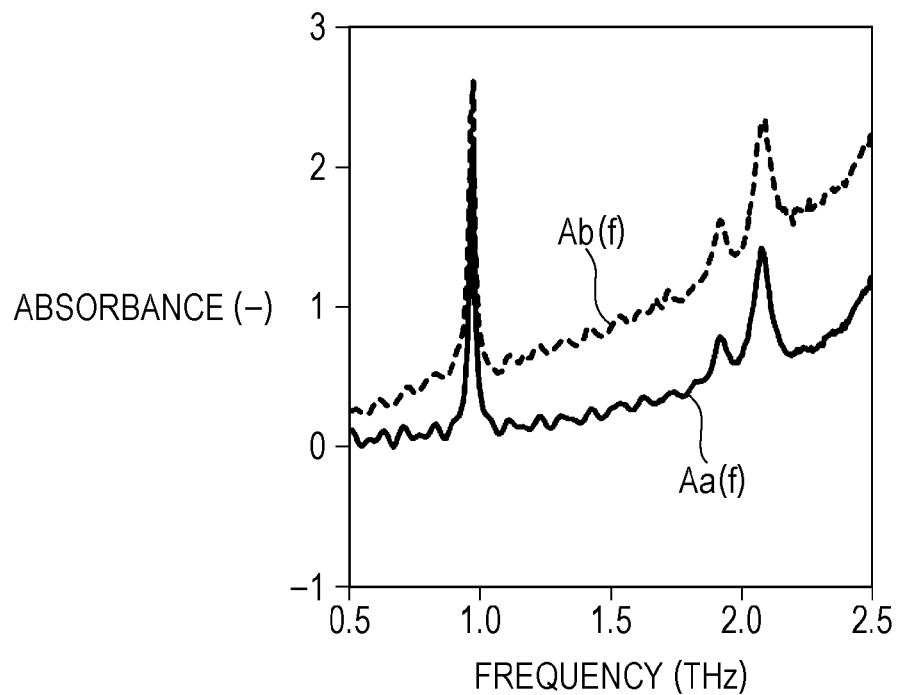
FIG. 17 is a graph showing an absorption spectrum Aa(f) of sample a and an absorption spectrum Ba(f) of sample b in Example 3.

A part of each of samples a and b was spread on a sample holder made of a polyethylene plate (10 mm in diameter) so as to have a uniform thickness. An absorption spectrum of each of samples a and b was calculated by irradiating each sample spread on the sample holder with a terahertz wave (irradiation spot of 3 mm in diameter) from the above. A result of absorption spectra Aa(f) and Ab(f) calculated in a frequency range from 0.5 THz to 2.5 THz is shown in FIG. 17. The absorption spectrum Aa(f) is indicated by a solid line, and the absorption spectrum Ab(f) is indicated by a broken line. Each of the absorption spectra showed a tendency that the absorbance as a whole increased as the frequency increased. Also, the gradient of the absorption spectrum Ab(f) of sample b was larger than the gradient of the absorption spectrum Aa(f) of sample a.

For each of sample a and sample b, three absorption bottoms were detected, and each of a baseline function Ba(f) and a baseline function Bb(f) as an exponential function was acquired by the least-square method as expressed by the formulas shown below.

$$Ba(f)=0.022 \cdot \exp[1.6 \cdot f] f : \text{frequency}$$

$$Bb(f)=0.18 \cdot \exp[0.99 \cdot f] f : \text{frequency}$$

Figure 18:
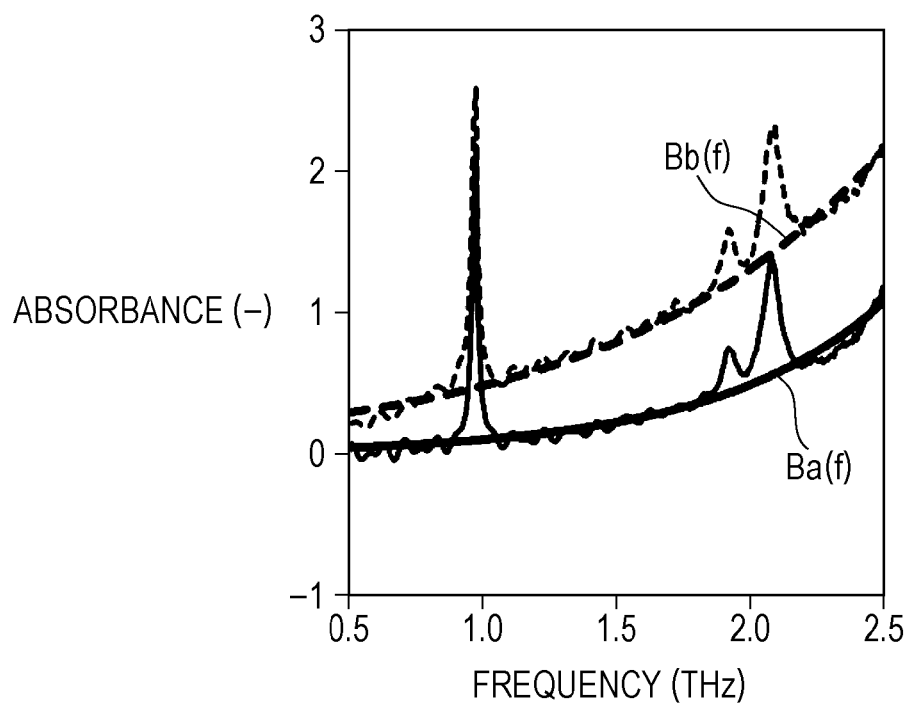
FIG. 18 is a graph showing the absorption spectrum Aa(f) and a baseline function Ba(f) of sample a, and the absorption spectrum Ba(f) and a baseline function Bb(f) of sample b in Example 3.

The absorption spectra Aa(f) and Ab(f) and the baseline functions Ba(f) and Bb(f) are shown in FIG. 18. Each of the absorption spectrum Aa(f) and the baseline function Ba(f) is indicated by a solid line, and each of the absorption spectrum Ab(f) and the baseline function Bb(f) is indicated by a broken line.

Next, post-subtraction spectrums Za(f) and Zb(f) were calculated by subtracting the baseline functions Ba(f) and Bb(f) from the absorption spectrums Aa(f) and Ab(f), respectively. The results expressed in an overlapped manner are shown in FIG. 19. The post-subtraction absorption spectrum Za(f) is indicated by a solid line, and the post-subtraction absorption spectrum Zb(f) is indicated by a broken line. The results shown in FIG. 19 are displayed on the display unit.

By displaying the post-subtraction spectrums, it was possible to visually determine that tyrosine contents of sample a and sample b were the same.

Example 4

When the post-subtraction spectrum is displayed, it is possible to inform a user of the result of the subtraction processing by displaying the values acquired by subtracting the baseline function from the absorption spectrum.

In the same manner as in Example 3, baseline functions Ba(f) and Bb(f) were calculated by measuring the absorption spectrums Aa(f) and Ab(f), and determining absorption bottoms. Then, post-subtraction spectrums Za(f) and Zb(f) were calculated by the subtraction processing.

Figure 20:
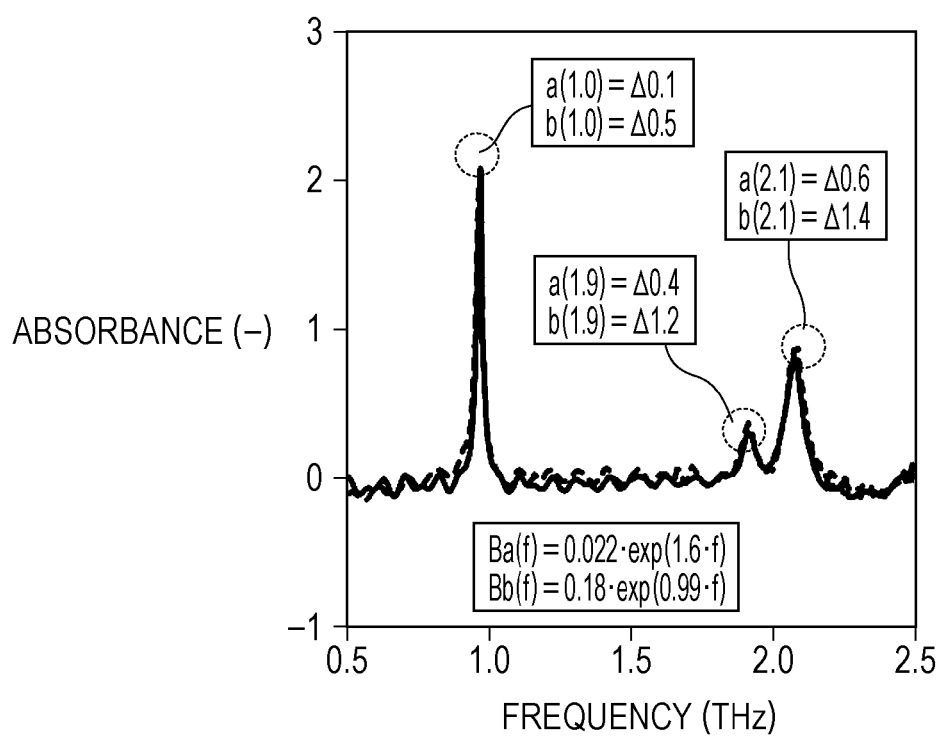
FIG. 20 is a graph showing a post-subtraction spectrum Za(f), a baseline function Ba(f) and subtracted values at peaks of sample a, and a post-subtraction spectrum Zb(f), a baseline function Bb(f) and subtracted values at peaks of sample b in Example 4.

In the present Example, absorption peaks were also calculated, and values of absorption peaks of the post-subtraction spectrums Za(f) and Zb(f) acquired by subtracting the baseline functions Ba(f) and Bb(f) from the absorption spectrums Aa(f) and Ab(f) were displayed. The result displayed together with the baseline functions Ba(f) and Bb(f) is shown in FIG. 20. In this manner of display, it is possible to visually recognize how much values are subtracted to acquire the post-subtraction spectrum.

Example 5

When the post-subtraction spectrum is displayed, it is possible to inform a user of the process of the subtraction processing by displaying which absorption bottoms were used to calculate the baseline function.

In the same manner as in Example 3, baseline functions Ba(f) and Bb(f) were calculated by measuring the absorption spectrums Aa(f) and Ab(f), and determining absorption bottoms. Then, post-subtraction spectrums Za(f) and Zb(f) were calculated by the subtraction processing.

Figure 21:
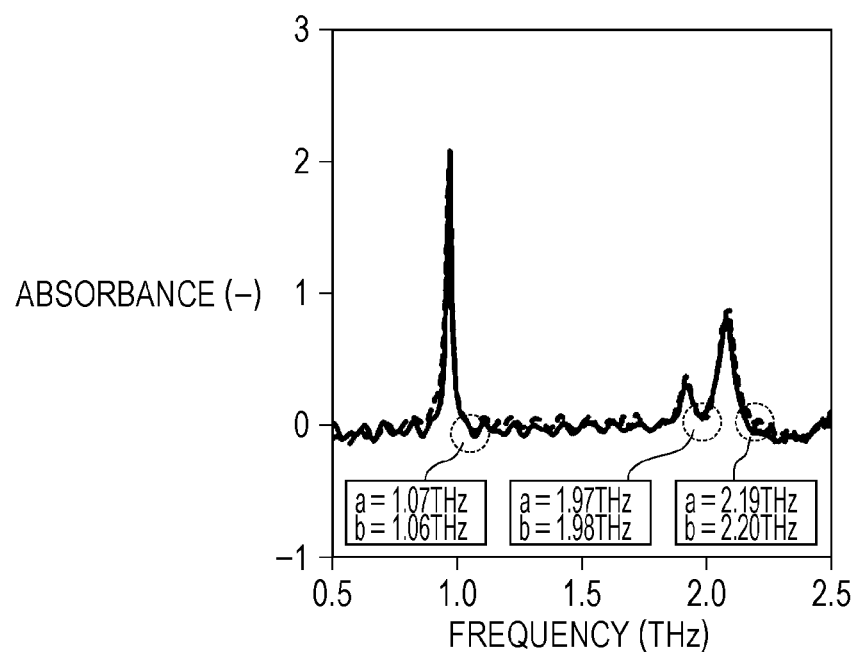
FIG. 21 is a graph showing a post-subtraction spectrum Za(f) and values at absorption bottoms of sample a, and a post-subtraction spectrum Zb(f) and values at absorption bottoms of sample b in Example 5.

Absorption bottoms determined to calculate the baseline function, displayed together with the post-subtraction spectrums Za(f) and Zb(f), are shown in FIG. 21. In this manner of display, it is possible to visually know which points were used to perform the processes of the subtraction processing.

Comparative Example

Referring to FIG. 23, all of the bottoms B11, B12, Bx and B13, each of which was detected as an area in which the derivative changed from a positive value to a negative value, were used to calculate the baseline function B(f). The baseline function B(f) was subtracted from the absorption spectrum A(f) to acquire a post-subtraction spectrum Z(f). Although the area from B12 to B13 should have been recognized as a single absorption peak, the area was recognized as two absorption peaks, one absorption peak from B12 to Bx, and the other from Bx to B13. Consequently, a correct identification result was not acquired.

The present disclosure provides a terahertz wave spectrometry system. More particularly, the present disclosure provides a terahertz wave spectrometry system that makes it possible to easily identify and quantitate an analyzing target molecule in an analyte, even if the analyte contains water, by calculating a baseline function expressing the absorption characteristic of water peculiar to the terahertz wave. In addition, the terahertz wave spectrometry system makes it possible to easily perform visual comparison between measurement results of a plurality of analytes.

REFERENCE SIGNS LIST 100 terahertz wave spectrometry system
101 terahertz wave emitter
102 light receiver
103 signal processor
104 analyte
200 terahertz wave spectrometry system
201 terahertz wave emitter
202 light receiver
203 signal processor
204 analyte
211 oscillation-side mirror
212 detection-side mirror
300 terahertz wave spectrometry system
301 terahertz wave emitter
302 light receiver
303 signal processor
304 analyte
310 display unit

What is claimed is:

1. A terahertz wave spectrometry system comprising:
a terahertz wave emitter for emitting a terahertz wave to irradiate a test substance with the terahertz wave;
a light receiver that receives an absorbance of a terahertz wave transmitted through or reflected from the test substance; and
a signal processor,
wherein the signal processor, in operation,
outputs an irradiation signal to the terahertz wave emitter to irradiate the test substance with the terahertz wave while increasing or decreasing a frequency f of the terahertz wave,
acquires an intensity of the terahertz wave received by the light receiver;
acquires a function A(f) of an absorption spectrum expressing the absorbance of the terahertz wave which has been transmitted through or reflected from the test substance with respect to the frequency f, on the basis of an intensity of the terahertz wave emitted by the terahertz wave emitter and the intensity of the terahertz wave received by the light receiver;
differentiates the function A(f) with respect to the frequency f to acquire a function A'(f);
detects two or more first areas in each of which a value of the function A'(f) changes from a negative value to a positive value as the frequency f increases;
defines bottom frequencies b1, b2, . . . , bm as values of the frequency f each satisfying a formula (I) below in an m-th one of the first areas, where m is an integer of 2 or more;

$$\text{function } A'(bm)=0 \tag{I}$$

calculates a value of the function A(bm) at each bottom frequency bm;
forms a baseline function B(f) passing through coordinates (b1, f(b1)), coordinates (b2, f(b2)), . . . , coordinates (bm, f(bm)), or a neighborhood of these coordinates; and
subtracts the baseline function from the absorption spectrum.

2. The terahertz wave spectrometry system according to claim 1, wherein
the signal processor, in operation,
detects two or more second areas in each of which the value of the function A'(f) changes from a positive value to a negative value as the frequency f increases;
defines peak frequencies p1, p2, . . . , pm as values of the frequency f each satisfying a formula (II) below in an m-th one of the second areas, where m is an integer of 2 or more;

$$\text{function } A'(pm)=0 \tag{II}$$

calculates a value of the function A(pm) at each peak frequency pm; and
excludes coordinates (bs, f(bs)) from coordinates used for forming the baseline function B(f) in a case where a formula (III) below is satisfied, $$f(ps)-f(bs)<g \tag{III}$$

where s is an integer of 2 or more and smaller than m, and g is a predetermined value.

3. The terahertz wave spectrometry system according to claim 2, wherein the predetermined value is 0.2.

4. The terahertz wave spectrometry system according to claim 2, wherein
the signal processor, in operation,
excludes the coordinates (bs, f(bs)) from the coordinates used for forming the baseline function B(f) in a case where a formula (IV) below is satisfied, $$|f(bs)-f(bs-1)| \geq c \tag{IV}$$

where s is an integer of 2 or more and smaller than m, and c is a predetermined value.

5. The terahertz wave spectrometry system according to claim 2, wherein
the signal processor, in operation,
excludes the coordinates (bs, f(bs)) from the coordinates used for forming the baseline function B(t) in a case where a formula (V) below is satisfied, $$|f(ps)-f(ps-1)|<d \tag{V}$$

where bs is larger than ps−1 and smaller than ps, s is an integer of 2 or more and smaller than m, and d is a predetermined value.

6. The terahertz wave spectrometry system according to claim 4, wherein
the signal processor, in operation,
excludes either coordinates (bs−1, f(bs−1)) or the coordinates (bs, f(bs)) from the coordinates used for forming the baseline function B(f) in a case where the formula (IV) is not satisfied and a formula (VI) below is satisfied, $$|f(bs)-f(bs-1)|<e \tag{VI}$$

where s is an integer of 2 or more and smaller than m, and e is a predetermined value.

7. The terahertz wave spectrometry system according to claim 1, wherein the signal processor, in operation,
sets, among the coordinates corresponding to the bottom frequencies, coordinates corresponding to a minimum frequency in a measuring frequency range as a minimum frequency bottom, and coordinates corresponding to a maximum frequency in the measuring frequency range as a maximum frequency bottom; and
calculates the baseline function so that the baseline function passes through at least both the minimum frequency bottom and the maximum frequency bottom.

8. The terahertz wave spectrometry system according to claim 7, wherein
the signal processor, in operation,
sets, among the coordinates corresponding to the bottom frequencies, coordinates located between the minimum frequency bottom and the maximum frequency bottom as an intermediate bottom; and
calculates the baseline function so that the baseline function passes through at least all of the minimum frequency bottom, the maximum frequency bottom and the intermediate bottom.

9. The terahertz wave spectrometry system according to claim wherein
the signal processor, in operation,
detect two or more second areas in each of which the value of the function $A'(f)$ changes from a positive value to a negative value as the frequency f increases;
define peak frequencies p1, p2, ..., pm as values of the frequency f each satisfying a formula (II) below in an m-th one of the second areas, where m is an integer of 2 or more;

$$\text{function } A'(p)=0 \tag{II}$$

calculate a value of the function $A(pm)$ at each peak frequency pm;

exclude coordinates (bs, f(bs)) from coordinates used for forming the baseline function B(f) in a case where a formula (III) below is satisfied, $$f(ps)-f(bs)<g \tag{III}$$

where ps is smaller than bs, s is an integer of 2 or more and smaller than m, and g is a predetermined value.

10. The terahertz wave spectrometry system according to claim 7, wherein the measuring frequency range has a range of at least 1 THz.

11. The terahertz wave spectrometry system according to claim 1, wherein the baseline function is an exponential function or a quadratic function.

12. The terahertz wave spectrometry system according to claim 1, wherein the terahertz wave is in a frequency range from 0.1 THz to 10 THz.

13. The terahertz wave spectrometry system according to claim 1, further comprising a display unit,
wherein
the signal processor calculates the baseline function form the absorption spectrum, and then subtracts the baseline function from the absorption spectrum to calculate a post-subtraction absorption spectrum, and
the display unit displays at least the post-subtraction absorption spectrum.

14. The terahertz wave spectrometry system according to claim 13, wherein the display unit displays the post-subtraction absorption spectrums of two or more kinds of the test substances so that baselines of the post-subtraction absorption spectrums are overlapped.

15. The terahertz wave spectrometry system according to claim 13, wherein the display unit displays values subtracted by the baseline function.

* * * * *